US009730817B2

United States Patent
Lee et al.

(10) Patent No.: US 9,730,817 B2
(45) Date of Patent: Aug. 15, 2017

(54) APPARATUS FOR MANUFACTURING SCAFFOLD AND SCAFFOLD MANUFACTURED BY THE SAME

(71) Applicants: KOREA INSTITUTE OF MACHINERY & MATERIALS, Daejeon (KR); PROTEK KOREA CO.,LTD., Daejeon (KR)

(72) Inventors: Junhee Lee, Daejeon (KR); Sua Park, Daejeon (KR); Wan-Doo Kim, Daejeon (KR); Seung-Ho Choi, Daejeon (KR)

(73) Assignees: KOREA INSTITUTE OF MACHINERY & MATERIALS, Daejeon (KR); PROTEK KOREA CO., LTD., Daejeon (KR)

( * ) Notice: Subject to any disclaimer, the term of this patent is extended or adjusted under 35 U.S.C. 154(b) by 891 days.

(21) Appl. No.: 14/145,013

(22) Filed: Dec. 31, 2013

(65) Prior Publication Data

US 2014/0236281 A1    Aug. 21, 2014

(30) Foreign Application Priority Data

Feb. 20, 2013    (KR) .................. 10-2013-0017921

(51) Int. Cl.
| | |
|---|---|
| *B29C 67/00* | (2017.01) |
| *A61F 2/82* | (2013.01) |
| *A61L 31/04* | (2006.01) |
| *A61F 2/91* | (2013.01) |
| *B29C 41/08* | (2006.01) |

(52) U.S. Cl.
CPC ............ *A61F 2/82* (2013.01); *A61L 31/04* (2013.01); *A61F 2/91* (2013.01); *A61F 2240/001* (2013.01); *B29C 41/085* (2013.01)

(58) Field of Classification Search
CPC . B29C 67/0085; B29C 67/0059; B33Y 10/00; B33Y 30/00
USPC ........................................ 425/375
See application file for complete search history.

(56) References Cited

U.S. PATENT DOCUMENTS

| | | | | |
|---|---|---|---|---|
| 7,625,198 B2 * | 12/2009 | Lipson | ............... | B29C 67/0055 425/169 |
| 9,126,366 B2 * | 9/2015 | Park | .................... | B29C 67/0059 |
| 2010/0034960 A1 * | 2/2010 | Kindaichi | ................. | A61F 2/91 427/2.25 |
| 2011/0287122 A1 * | 11/2011 | Kim | ..................... | C12N 5/0062 425/174.8 R |
| 2011/0309614 A1 | 12/2011 | Guest | | |

FOREIGN PATENT DOCUMENTS

| | | |
|---|---|---|
| KR | 100473554 B1 | 3/2005 |
| KR | 20090064617 A | 6/2009 |
| WO | 2007074896 A1 | 7/2007 |

* cited by examiner

*Primary Examiner* — Joseph S Del Sole
*Assistant Examiner* — Thukhanh T Nguyen
(74) *Attorney, Agent, or Firm* — Hauptman Ham, LLP

(57) ABSTRACT

In an apparatus for manufacturing a scaffold and a scaffold manufactured by the apparatus, a collector is disposed under a dispensing head that dispenses melted bio materials (polymer) for manufacturing the scaffold. The collector has a cylindrical tube shape. Both sides of the tube shape are fixed. Thus, the tube is securely fixed and bending of the tube is prevented. Also, accuracy and preciseness of the scaffold are improved.

12 Claims, 13 Drawing Sheets

APPARATUS FOR MANUFACTURING SCAFFOLD AND SCAFFOLD MANUFACTURED BY THE SAME

PRIORITY STATEMENT

This application claims priority under 35 U.S.C. §119 to Korean Patent Application No. 10-2013-0017921, filed on Feb. 20, 2013 in the Korean Intellectual Property Office (KIPO), the contents of which application are herein incorporated by reference in their entirety.

BACKGROUND

1. Field of Disclosure

The present disclosure of invention relates to an apparatus for manufacturing a scaffold and a scaffold manufactured by the same. More particularly, the present disclosure of invention relates to an apparatus for manufacturing a tube shaped scaffold, which has a tube fixing structure that is capable of fixing a tube to prevent the tube from being bent and to securely fixing the tube, and a scaffold manufactured by the same.

2. Description of Related Technology

Tissue engineering is technologies for manufacturing a substitute of a tissue to transplant the substitute into a living body based on basic concepts and technologies of bioscience, medical science and engineering, thereby maintaining, improving and recovering body function. In 1980's, artificial skin was firstly invented so that the tissue engineering was recognized as one of new studies. The tissue engineering has actively studied in various fields until recently. When a structure of the tissue is very complex, the study for the complex tissue is in an early stage. However, when a structure of the tissue such as skin, bone, etc., is simple, the substitute has been improved to be widely used.

In order to realize the tissue engineering, a portion of tissue is extracted from a body of a patient. Cells are separated from the extracted tissue. The separated cells are cultivated to a required amount, thereby forming a scaffold that supports the cultivated cells. The scaffold is transplanted into the body. In most tissues and organs, the transplanted cells receive oxygen and nutrition by diffusion of body fluid until new blood vessel is formed. After the blood vessel is formed, the cells multiply and differentiate to form new tissue and organ, and the scaffold that is biolytic is dissolved, thereby disappearing.

The scaffold has various shapes for various portions of the body. One of the various shapes of the scaffold is a tube shape. The tube shaped scaffold is used for the substitute for tissues such as the blood vessel, nerve, etc. In order to manufacture the conventional tube shaped scaffold, a base frame having the tube shape is fixed, and then the base frame is rotated to float materials of the scaffold on the base frame.

In order to manufacture the tube shaped scaffold, a base frame having the tube shape is required to be fixed. Various apparatus for fixing ends of the cylindrical shaped rod or tube has been studied. A structure of the apparatus for fixing may be changed based on diameter, material, strength or flexibility, use, etc. The tube for a base frame of the tube shaped scaffold is thin and has small strength.

In order to fix the tube, an apparatus of FIGS. 1A and 1B is used. Referring to FIGS. 1A and 1B, a pair of corn shaped supporting parts 5000 are inserted into both ends of a tube 1000 of a conventional apparatus 5 for fixing a tube. An apex of the corn shaped supporting part 5000 is inserted into the tube 1000 until an outer diameter of the corn shaped supporting part 5000 is substantially the same as an inner diameter of the tube 1000. When the corn shaped supporting part 5000 is accurately inserted into the both sides of the tube 1000, the tube is fixed and supported and the corn shaped supporting part 5000 is rotatable. Thus, the tube 1000 may be rotated by a rotating part such as a motor combined with the corn shaped supporting part 5000.

However, the conventional apparatus 5 for fixing the tube has the following problems. FIGS. 2A and 2B are perspective views illustrating the problems of the conventional apparatus for fixing the tube. In order to fix the tube 1000 of the conventional apparatus 5 for fixing the tube, the corn shaped supporting part 5000 is inserted into the both ends of the tube 1000. However, when the corn shaped supporting part 5000 is not sufficiently inserted in the tube 1000 (shown in FIG. 2A), the tube 1000 may not be fixed. Thus, although the corn shaped supporting part 5000 is rotated, the tube 1000 may not be rotated and may skid. In contrast, when the corn shaped supporting part 5000 is inserted into the tube 1000 at an excessive strength (shown in FIG. 2B), the tube 1000 may be bent. The tube 1000 is sued for the base frame for manufacturing the tube shaped scaffold, and the tube 1000 may have a diameter of several to several tens of millimeters and a length of several hundred millimeters. Thus, when the corn shaped supporting part 5000 presses the both ends of the tube 1000 by the excessive strength, the tube 1000 may be easily bent. When the tube 1000 is bent, the tube 1000 is dislocated from a right position so that accuracy of floating process of the manufacturing the scaffold or the floating process may be impossible.

Various apparatuses for fixing the tube have been disclosed. Structures for fixing the tube are disclosed in related arts. Korean Patent Registration No. 0473554 discloses "Tool Carrier Device Of Machining Center" on Feb. 17, 2005. U.S.A. laid open publication No. 2011-0309614 discloses "Tube Coupling" on Dec. 22, 2011. However, the structure of the apparatus for fixing the tube is required to be changed based on the diameter, material, strength or flexibility, usage, etc. Thus, the apparatus for fixing the tube of the above-mentioned related arts is not suitable for fixing the tubes. In particular, the apparatus for fixing the tube of the related arts fixes only one end of the tube so that the related art does not mention or disclose the bending or skid of the tube. Also, the tube of the related art is strong so that the tube may not be deformed. Thus, the apparatus of the related art may not be applied to the thin and weak tube of FIGS. 1A to 2B.

Also, there are several related arts concerning the tube shaped scaffold. Korean Patent laid open publication No. 2009-0064617 discloses "Method For Fabrication Bio-Degradable Polymer Nerve Conduit With Biodegradable Plastic/Nano Microfibrous Scaffold" on Jun. 22, 2009. International Patent laid open publication No. WO07/074896 discloses "Composite Scaffold For Tissue Regeneration" on Jul. 5, 2007. However, the above-mentioned related arts also do not mention or disclose the above-mentioned problems. Any solution for the above-mentioned problems may be insoluble.

SUMMARY

The present invention is developed to solve the above-mentioned problems of the related arts. The present invention provides an apparatus for manufacturing a scaffold, which has a collector disposed under a dispensing head that dispenses melted bio materials (polymer) for forming a scaffold and having a cylindrical tube shape and fixes the tube from both ends of the collector, to securely fix the tube and to prevent the tube from being bent.

The present invention also provides a scaffold manufactured by the above-mentioned apparatus for manufacturing the scaffold, which has improved accuracy and preciseness.

According to an exemplary embodiment, an apparatus for manufacturing a scaffold includes a dispensing head 100, a collector 200, a dispensing position controller 300 and a collecting position controller 400. The dispensing head 100 includes a liquid storing part 110, a nozzle part 120 and a heating part 130. The liquid storing part 110 stores melted bio materials (polymer). The nozzle part 120 dispenses the melted bio materials (polymer) supplied from the liquid storing part 110. The heating part 130 controls temperature of the melted bio materials (polymer) stored in the liquid storing part 110. The collector 200 has a cylindrical shape. The collector 200 is disposed under the dispensing head 100 to collect the melted bio materials (polymer) dispensed through the nozzle part 120. The dispensing position controller 300 transports the dispensing head 100 or the collector 200 in a direction selected from the group consisting of an X direction, a Y direction and a Z direction to control dispensing position. The collecting position controller 400 includes a pair of supporting parts 410, a pair of fixing parts 420, a transporting part 430 and a rotating part 440. The supporting parts 410 are spaced apart from each other in an extending direction of the collector 200. The fixing parts 420 are disposed on the supporting parts 410, respectively. The fixing parts 420 holds and fixes both ends of the collector 200. The transporting part 430 transports at least one of the supporting parts 410 in the extending direction of the collector 200. The rotating part 440 is disposed at least one of the fixing parts 420 to rotate the collector 200 along the extending direction as an axis. The fixing part 420 of the collecting position controller 400 may hold and fix the both ends of the collector 200, and the transporting part 430 may transport at least one of the supporting parts 410 so that a distance between the supporting parts 410 may be increased along the extending direction of the collector 200, so that a pulling tension may be applied to the collector 200 in the extending direction and the both ends of the collector 200 may be holded and fixed.

In an embodiment, each of the supporting parts 410 of the collecting position controller 400 may be protruded in the extending direction of the collector 200 to form a receiving portion 415 having an empty space, and the fixing part 420 may include a collet 421 and a clamper 422. The collet 421 may have one side, into which the collector 200 is inserted, and another side received in and supported by the receiving portion 415. The clamper 422 may support the one side of the collet 421 and combined with the receiving portion 415 so that the collet 421 may be received in and fixed to the receiving portion 415. Thus, the collector 200 may be inserted into the collet 421 and the receiving portion 415 may be combined with the clamper 422, thereby fixing and holding the collector 200.

In an embodiment, a receiving screw 415*a* may be formed on an outer surface of the receiving portion of the collecting position controller 400, and a clamping screw 422*a* corresponding to the receiving screw 415 may be formed on an inner surface of the clamper 422 corresponding to the receiving portion 415. Thus, the receiving screw 415*a* may be combined with the clamping screw 422*a* by a screw combination, thereby combining the receiving portion 415 to the clamper 422.

In an embodiment, the one side of the collet 421 of the collecting position controller 400 may include a collet head 421*a* having a cross-sectional diameter that decreases as a distance from a periphery is decreased to form a tapered shape, and a clamping tapered portion 422*b* formed on an inner surface of an opposite side to the receiving portion 415 of the clamper 422, and having an inclined inner surface corresponding to the collet head 421*a*. The another side of the collet 421 may include a collet tail 421*b* of which a diameter of an inner surface is decreased, as a distance from the periphery is decreased, and a receiving tapered portion 415*b* formed on an inner surface of the receiving portion 415 and having an inclined surface corresponding to the collet tail 421*b*. Thus, the collet head 421*a* and the collet tail 421*b* may be pressed to make contact with the clamping tapered portion 422*b* and the receiving tapered portion 415*b*, respectively, when the receiving portion 415 is combined with the clamper 422 so that the collet 421 is compressed.

In an embodiment, the fixing part 420 of the collecting position controller 400 may include at least two divided subparts 423 that are dividable in a radial direction with respect to an extending direction of the collector 200 as an axis. The divided subparts 423 may be combined to form the fixing part 420 having a receiving portion 424, and a hook 425 may be protruded at an entry of the receiving portion 424. Thus, the collector 200 may be disposed in a position corresponding to the receiving portion 424 while the divided subparts 423 are separated, and then the divided subparts 423 may be combined so that the hook 425 may hold the collector 200 to fix the collector 200.

In an embodiment, the receiving portion 424 may have a diameter substantially equal to or smaller than the collector 200. The collector 200 may have a recess corresponding to the hook 425.

In an embodiment, the collecting position controller 400 may fix the collector 200 that has a ratio of diameter to length to be about 0.05 to about 0.5.

In an embodiment, the liquid storing part 110 may store melted bio materials (polymer) that is formed by melting or liquefying bio compatible material.

In an embodiment, the collector 200 may be replaceable with another collector 200 having different diameter.

In an embodiment, the apparatus for manufacturing the scaffold may further include a controller 500 connected to the dispensing position controller 300 to control dispensing position, and connected to the collecting position controller 400 to control speed of rotation of the fixing part 420.

According to an exemplary embodiment, a scaffold is manufactured by the above-mentioned apparatus.

In an embodiment, the scaffold 5000 may include at least two layers of strand overlapped in radial and X directions of the collector 200 and having different shapes. The scaffold 5000 may include a first layer 610 of strand, a second layer 620 of strand and a third layer 630 of strand. The first layer 610 of strand may be continuously or discontinuously formed along an outer surface of the collector 200 in a radial direction of the collector 200. The second layer 620 of strand may be repeatedly formed along the outer surface of the collector 200 in an X direction to have a plurality of linear shapes that are spaced apart from each other in the radial direction of the collector 200. The third layer 630 of strand may be formed on the outer surface of the collector 200 and having no pores in a surface.

In an embodiment, the first and second layers 610 and 620 of strands of the scaffold 5000 may be overlapped with each other to form a net type dispensed portion 640 that are disposed at least one of an inner surface and an outer surface of the third layer 630 of strands which has no pores in the surface.

According to an exemplary embodiment, a scaffold 5000 manufactured by the above-mentioned apparatus 1000 is used to manufacture a stent from a bio compatible material stored in the liquid storing part 110.

According to the apparatus for manufacturing the tube shaped scaffold of the present invention, the apparatus for manufacturing the tube shaped scaffold of the present invention is different from the conventional apparatus for manufacturing the tube shaped scaffold which fixes a thin tube. The conventional apparatus pushes both sides of the tube to fix the tube. In contrast, the apparatus for manufacturing the tube shaped scaffold of the present invention pulls the both sides of the tube to fix the tube, so that the tube may be securely fixed and bending of the tube is prevented.

Thus, when a material is floated on the tube, the tube is securely fixed so that operation of the apparatus for manufacturing the tube shaped scaffold is stabilized although the tube is rotated. Also, the bending of the tube is prevented so that inaccuracy of manufacturing or impossibility of manufacturing caused by the bending of the tube, which may be caused by dislocation of the tube, is prevented. In addition, preciseness of the manufacturing is improved.

That is, although the tube is thin, the preciseness and accuracy of the manufacturing are greatly improved. Thus, highly flex material such as plastic may be used as the tube, so that various manufacturing processes may be possible and scope of subjects for manufacturing may be greatly increased.

The apparatus for manufacturing the scaffold precisely and securely fixes the collector without deformation of the collector so that the scaffold may have precise shape. Thus, quality such as preciseness, accuracy, etc., of the scaffold may be greatly improved. Also, the apparatus for manufacturing the scaffold may be used for manufacturing various shaped scaffold as well as the tube shaped scaffold. In addition, the apparatus for manufacturing the tube shaped scaffold may be applied to vessel, nerve, tear duct, stent, etc.

BRIEF DESCRIPTION OF THE DRAWINGS

The above and other features and advantages will become more apparent by describing exemplary embodiments thereof with reference to the accompanying drawings, in which.

DETAILED DESCRIPTION

Hereinafter, exemplary embodiment of the invention will be explained in detail with reference to the accompanying drawings.

Figure 3:
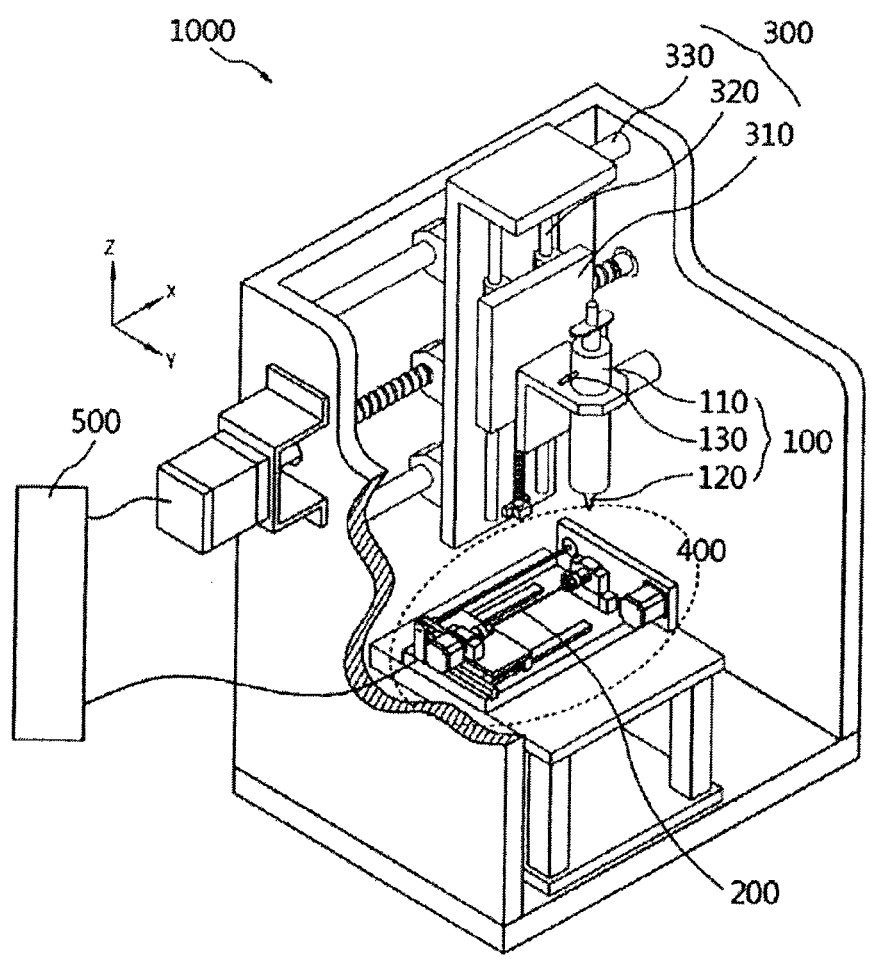
FIG. 3 is a partially cut-out perspective view illustrating an apparatus for manufacturing a scaffold according to one example embodiment of the present invention.

FIG. 3 is a partially cut-out perspective view illustrating an apparatus for manufacturing a scaffold according to one example embodiment of the present invention. Referring to FIG. 3, the apparatus 1000 for manufacturing the scaffold includes a dispensing head 100, a collector 200, a dispensing positing controller 300 and a collecting position controller 400.

The dispensing head 100 includes a liquid storing part 110, a nozzle part 120 and a heating part 130. Bio compatible material is liquefied or melted in the liquid storing part 110. The melted bio materials (polymer) supplied from the liquid storing part 110 is dispensed through the nozzle part 120. The heating part 130 controls temperature of the melted bio materials (polymer) stored in the liquid storing part 110. Examples of the bio compatible material may include bio compatible polymer, bio material, bio protein, etc. The solution storing part 110 is heated by the heating part 130 so that the melted bio materials (polymer) stored in the liquid storing part 110 may be liquefied or melted. The apparatus 1000 for manufacturing the scaffold stores the bio compatible material in the liquid storing part 110 as the melted bio materials (polymer) state to manufacture the scaffold 5000 having various types such as tear duct, nerve, vessel, etc. Also, the product manufactured from the bio compatible material stored in the liquid storing part 110 may be used for the stent.

The collector 200 has a cylindrical shape (or a tube shape) and is disposed under the dispensing head 100. Thus, the melted bio materials (polymer) that is dispensed through the nozzle part of the dispensing head 100 may be collected.

The dispensing position controller 300 transports the dispensing head 100 in an X direction, a Y direction and a Z direction to control dispensing position. In FIG. 3, the dispensing position controller 300 includes a fixing bracket 310, an X guide rail 330 and a Y guide rail 340. A Z guide rail 320 is disposed on the fixing bracket 310. The Z guide rail 320 guides transportation of the dispensing head in the Z direction. The X guide rail 330 guides transportation of the dispensing head in the X direction. The Y guide rail 340 guides transportation of the dispensing head in the Y direction. However, the present invention is not limited by the above-mentioned structure. For example, the collector 200 may be transported in the X, Y and Z directions to control the dispensing position. In the present invention, relative location between the dispensing head 100 and the collector 200 is controlled based on three degrees of freedom in three directions. Thus, the dispensing position controller 300 may have various structures.

The collecting position controller 400 solves the problem of the conventional apparatus, in which the collector 200 having the tube shape may be bent or skid caused by inaccurate fixing of the conventional collecting position controller. The collecting position controller 400 will be explained in detail with reference to FIGS. 4 and 5.

Referring again to FIG. 3, the apparatus 1000 for manufacturing the scaffold may further include a controller 500. The controller 400 is connected to the dispensing position controller 300 to control the dispensing position, and is connected to the collecting position controller 400 to control speed of rotation of a fixing part 420. Thus, the apparatus 1000 for manufacturing the scaffold controls the dispensing position of the dispensing head 100 and the speed of the rotation of the fixing axes so that the scaffold may have various shapes.

The collector 200 of the apparatus 1000 for manufacturing the scaffold may be substituted by any collector having different diameters. For example, the diameter of the collector 200 may be about 1 mm to about 20 mm. Thus, the scaffold 5000 may have various sizes suitable for the tear duct, the vessel, the nerve, etc.

Hereinafter, the collecting position controller 400 will be explained in detail.

Figure 4:
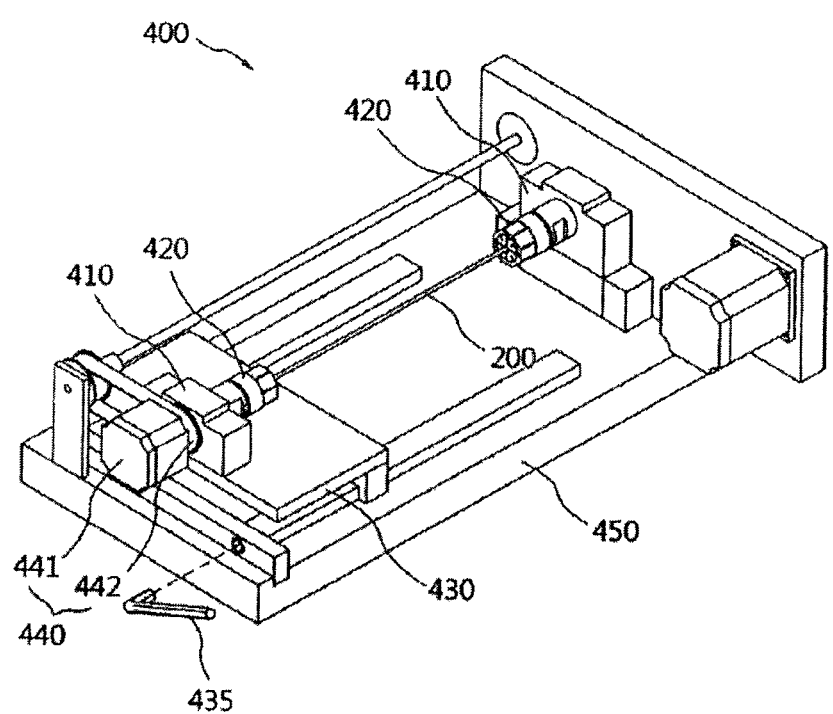
FIG. 4 is a perspective view illustrating a collecting location controller according to one example embodiment of the present invention.
Figure 5:
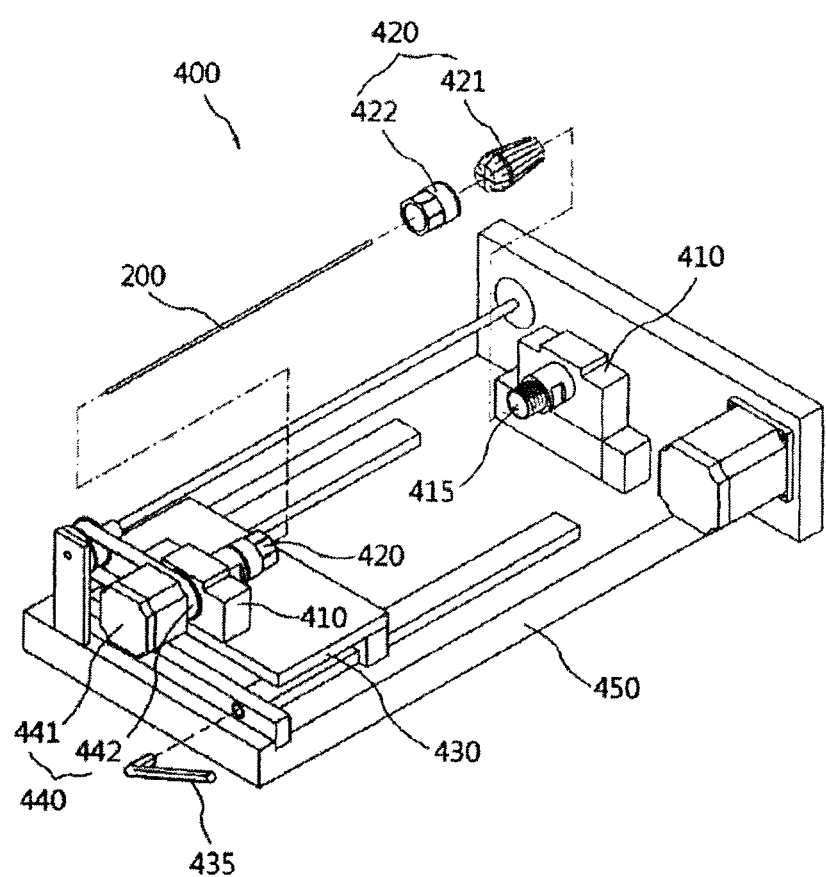
FIG. 5 is an exploded perspective view illustrating the collecting location controller of FIG. 4.

FIG. 4 is a perspective view illustrating a collecting location controller according to one example embodiment of the present invention. FIG. 5 is an exploded perspective view illustrating the collecting location controller of FIG. 4. Referring to FIGS. 4 and 5, the collecting position controller 400 includes a supporting part 410, a fixing part 420, a transporting part 430 and a rotating part 440. The collecting position controller 400 may further include a base 450 that collects and supports the supporting part 410, the fixing part 420, the transporting part 430 and the rotating part 440.

The collecting position controller 400 may further include a pair of the supporting parts 410. The supporting parts 410 are alternately arranged in an extension direction of the collector 200. The fixing part 420 is disposed on each of the supporting parts 410 to holds each of both ends of the collector 200 to fix the collector 200. The transporting part 430 transports at least one of the supporting parts 410 in the extension direction of the collector 200. In FIG. 4, the transporting part 430 is disposed on one of the supporting part 410 to slide on a rail structure. Alternatively, the transporting part 430 may have various structures. For example, the transporting part 430 may transport both of the supporting parts 410, and may have various structures such as a linear actuator, a motor, a rack gear, etc., for spacing the supporting parts 410. In FIG. 4, the transporting part 430 transports the supporting part 410 using a hexa lench 435. Alternatively, the transporting part 430 may transport the supporting part 410 using various elements.

The rotating part 440 is disposed on one side of the fixing part 420 to rotates the collector 200 along the extending direction of the collector 200 as an axis. The fixing part 420 rotates with respect to the supporting part 410 so that the rotating part 440 rotates the fixing part 420. The rotation of the fixing part 420 is transmitted to the collector 200 so that the collector 200 rotates with the fixing part 420. In particular, the rotating part 440 may include a motor 441 and a pulley 442. Alternatively, the rotating part 440 may have various structures for fixing and rotating the collector 200.

The main point of the collecting position controller 400 will be explained in detail. The collecting position controller 400 holds the both ends of the collector 200 to fix the collector 200. The collecting position controller 400 transports the supporting part 410 so that the distance between the supporting parts 410 is increased along the extending direction of the collector 200. The collecting position controller 400 applies tension to the collector 200 on both sides along the extending direction of the collector 200, and holds the both ends of the collector 200 to fix the collector 200.

Figure 1A:
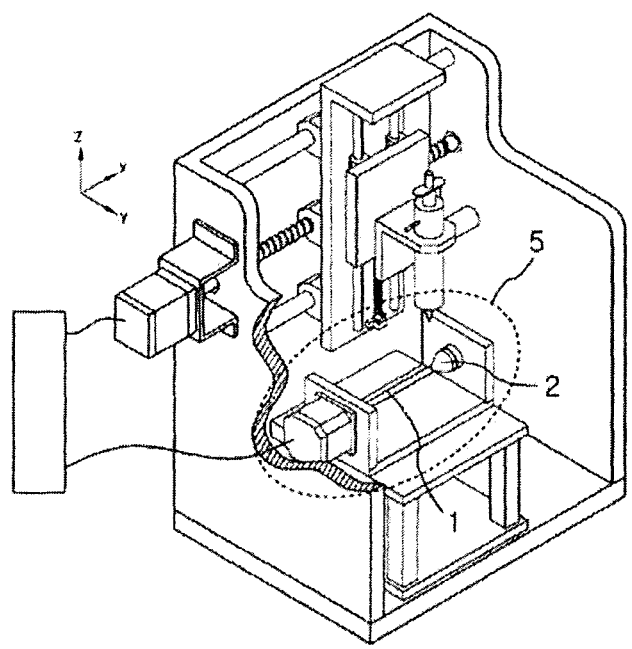
FIGS. 1A and 1B are perspective views illustrating a conventional apparatus for fixing a tube.
Figure 1B:
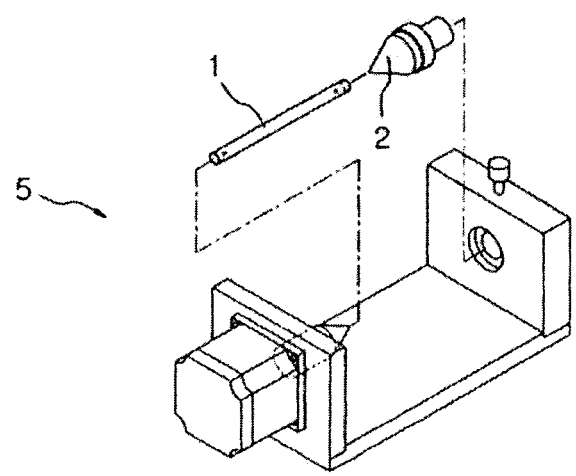
Figure 2A:
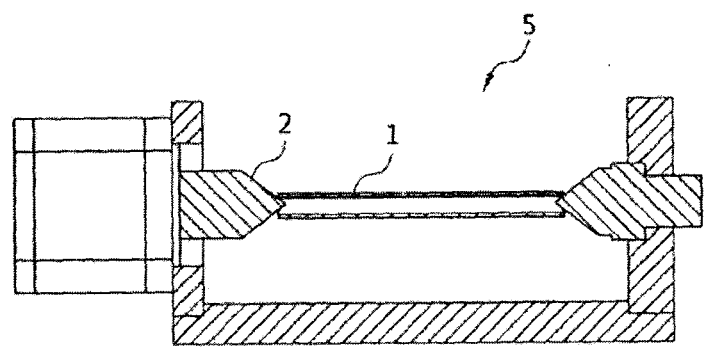
FIGS. 2A and 2B are perspective views illustrating the problems of the apparatus shown in FIG. 1B.
Figure 2B:
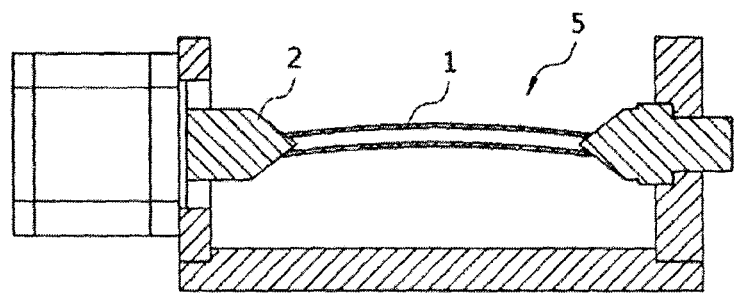

In the conventional collecting position controller of FIGS. 1A and 1B, the corn shaped supporting part is inserted into each of the both sides of the tube to pull the tube, thereby fixing the tube. The tube is transported along the corn shaped supporting part by pulling the tube so that the tube is centered with respect to the corn shaped supporting part. However, the conventional collecting position controller has the problems of FIGS. 2A and 2B. That is, when the tube is not sufficiently pulled, the tube is not fixed (shown in FIG. 2A). Also, when the tube is excessively pulled, the tube is bent (shown in FIG. 2B). When the tube is insecurely fixed, the tube may not stably rotate, thereby accuracy of process is greatly deteriorated.

Figure 6A:
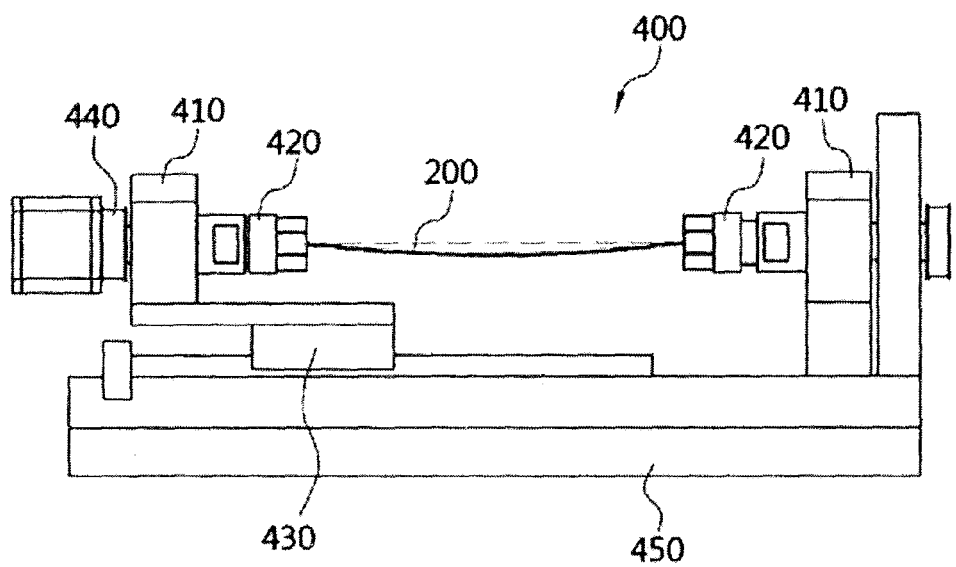
FIGS. 6A and 6B are cross-sectional views illustrating fixing a tube of FIG. 4.
Figure 6B:
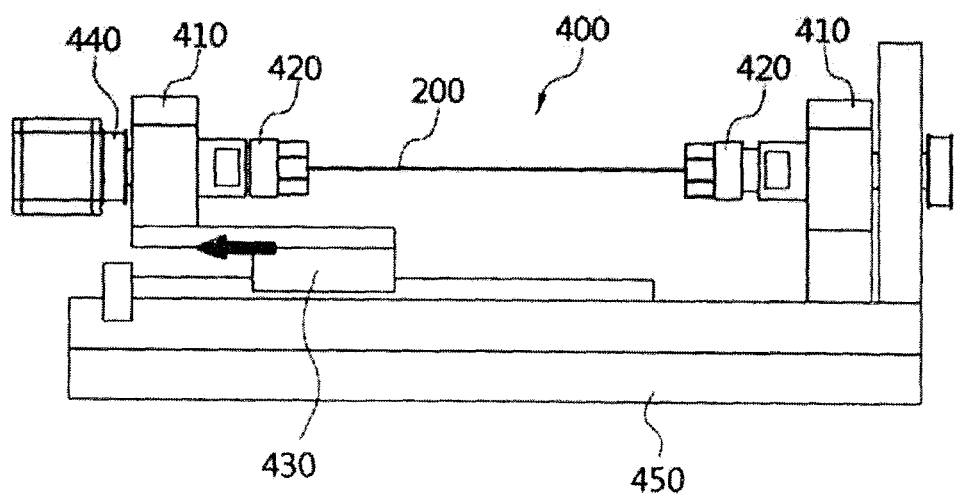

However, the collecting position controller 400 of the present invention has different structure from the conventional collecting position controller of FIGS. 1A to 2B. That is, the collecting position controller 400 holds the both sides of the collector 200 to fix the collector 200, so that the tension is applied to the both ends of the collector 200. FIGS. 6A and 6B are cross-sectional views illustrating fixing a tube of FIG. 4 using the collecting position controller 400. For example, the collecting position controller 400 may fix the collector 200 having a diameter of about 0.5 mm to about 50 mm and a length of about 100 mm. When the both ends of the collector 200 are holded, the collector 200 may be bent downwardly by a gravitational force (shown in FIG. 6A). The collecting position controller 400 holds the both ends of the collector 200, and the transporting part 430 of the collecting position controller 400 is transported to apply the tension to the both ends of the collector 200. Thus, the downward bending caused by the gravitational force may be compensated so that the collector 200 has a straight shape.

When the collector 200 having the tube shape is pulled, the collecting position controller 400 solves the above-mentioned problems of the conventional collecting position controller. Also, when the collector 200 is pulled to be fixed, the collector 200 may be securely fixed. Thus, the collector 200 may be easily rotated.

The problems of the skid and the bending caused by the inaccurate fixing limited processes using the tube. However, the collecting position controller 400 of the present invention solves the above-mentioned problems, so that the processes using the tube may be used in various fields. For example, in order to manufacture the tube shaped scaffold, the tube is used as a base frame and the material is floated on the tube. During the floating of the material on the tube, minute control of the rotation and position of the tube is required. The collecting position controller 400 securely fixes the tube and prevents the bending of the tube, thereby improving productivity of the processes. The collecting position controller 400 securely fixes the tube and prevents bending of the tube, so that productivity may be improved. The collecting position controller 400 securely fixes the tube so that the collecting position controller 400 may freely control the rotation of the tube and may prevent the bending of the tube. Thus, error in detecting position of the tube is prevented, so that preciseness of controlling of the process is improved. The conventional collecting position controller has the above-mentioned problems such as the insecure fixing and the bending of the tube, so that minute pattern may not be formed on a tube shaped subject. However, the collecting position controller 400 of the present invention may form the minute pattern on the tube shaped subject as well as the tube shaped scaffold, so that the apparatus 1000 may be used in various fields.

Figure 7A:
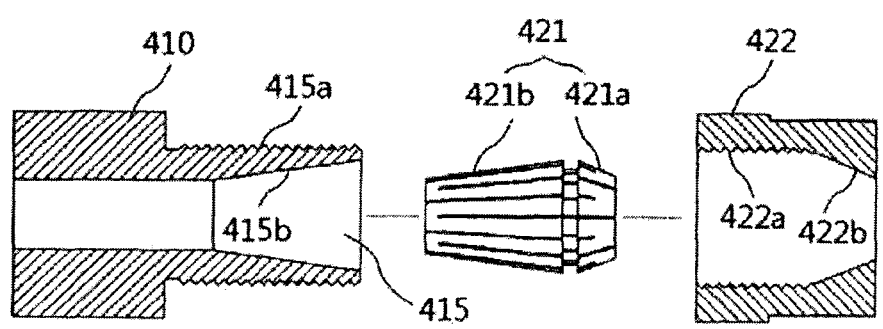
FIGS. 7A and 7B are cross-sectional views illustrating a fixing part of FIG. 4.
Figure 7B:
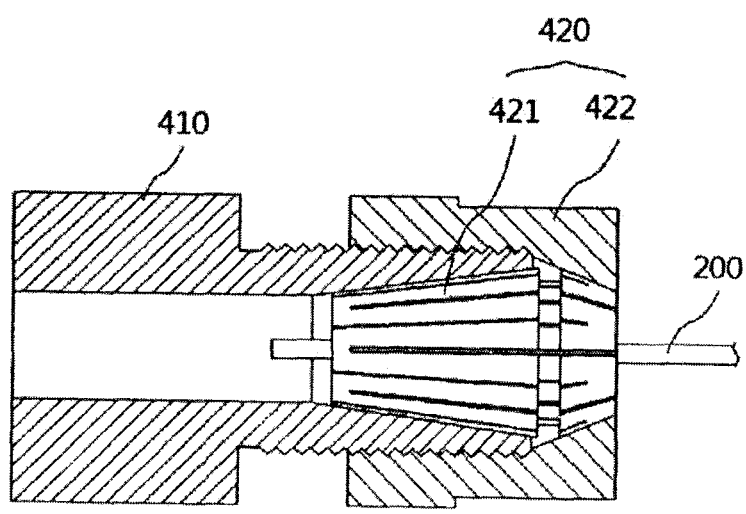

FIGS. 7A and 7B are cross-sectional views illustrating a fixing part of FIG. 4. Referring to FIGS. 7A and 7B, the fixing part 420 has a fixing structure of a collet shape. In particular, the fixing structure of the collecting position controller 400 includes a receiving portion 415 formed on the supporting portion 410, a collet 421 and a clamper 422 formed on the fixing part 420. The collet typed fixing structure has high fixing strength to be used in a tool fixing structure of a machine tool. Hereinafter, the structure of the fixing part 420 will be explained.

Referring to FIG. 7A, the receiving portion 415 is disposed on each of the pair of the supporting parts 410. The receiving portion 415 is protruded in the extending direction of the collector 200 to form an empty space. The collet 421 is received in the empty space of the receiving portion 415. The collector 200 is received in one side of the collet 421, and another side of the collet 421 is received in the receiving portion 415. The clamper 422 supports one side of the collet 421 so that the collet 421 is received in and combined with the receiving portion 415.

In the fixing part 420 of FIG. 7B, the collector 200 is inserted in the collet 421. The collet 421 having the collector 200 is received in the receiving portion 415. The receiving portion 415 is combined with the clamper 422 so that the collet 421 clamps the collector 200. Thus, the fixing part 420 fixes the collector 200.

The combining structure of the receiving portion 415 and the clamping 422 will be explained in detail. A receiving screw 415*a* is formed on an outer surface of the receiving portion 415. A clamper screw 422*a* is formed on an inner surface of the clamper 422 that is combined with the receiving portion 415. Thus, the clamper 422 is screwed into the receiving portion 415 so that the receiving screw 415*a* is screw combined with the clamper screw 422*a*. The receiving portion 415 is securely combined with the clamper 422 by the screw combination.

The clamping structure of the receiving portion 415 and the clamper 422, in which the collet 421 clamps and fixes the collector 200, will be explained in detail. The collet 421 has a collet head 421*a* having a tapered inner surface, a clamping tapered portion 422*b* and a receiving tapered portion 415*b*. A cross-sectional diameter of the tapered inner surface of the collet head 421*a* is decreased as a distance from a periphery of the collet head 421 is decreased. The clamping tapered portion 422*b* is formed on opposite side to the receiving portion 415 of the clamper 422, and has an inclined inner surface corresponding to the collet head 421*a*. Also, an opposite side of the collet 421 has a collet tail 421*b*. A diameter of an inner surface of the collet tail 421*b* is decreased, as a distance from a periphery of the collet 421 is decreased. The receiving tapered portion 415*b* is formed on an inner surface of the receiving portion 415, and has an inclined surface corresponding to the collet tail 421*b*. Thus, when the receiving portion 415 is combined with the clamper 422, the collet head 421*a* and the collet tail 421*b* are pressed to make contact with the clamping tapered portion 422*b* and the receiving tapered portion 415*b*, respectively, so that the collet 421 is compressed. When the receiving portion 415 is loosely combined with the clamper 422, the collet 421 is not compressed so that the collector 200 may be easily inserted into the fixing part 420. When the combination between the receiving portion 415 and the clamper 422 is tightened, the collet 421 is compressed along the collet 421 is pushed to be transported along the tapered portion. Thus, the collector 200 inserted into the collet 421 is clamped to be tightly fixed.

The above-mentioned structure has enough strength suitable for fixing elements of a machine tool. Thus, when the collector 200 is fixed using the above-mentioned structure, the collector 200 is securely fixed. Also, the tension is applied to the both ends of the collector 200 to prevent bending of the collector 200.

Figure 8A:
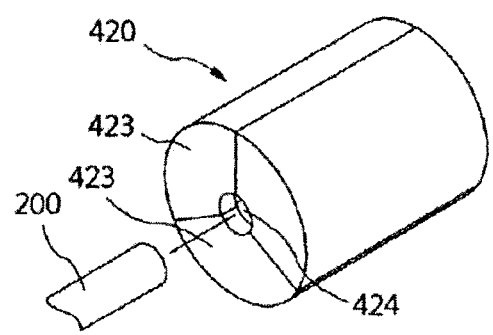
FIGS. 8A to 8C are perspective views illustrating a fixing part of a collecting position controller according to another example embodiment of the present invention.
Figure 8B:
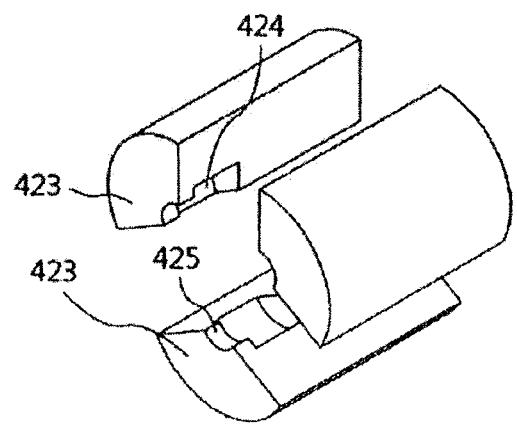
Figure 8C:
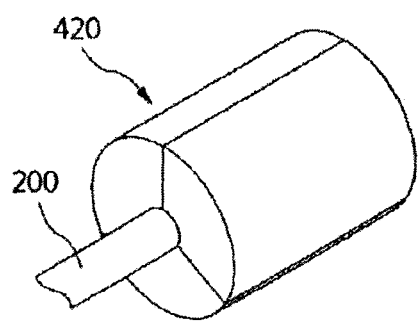
Figure 9A:
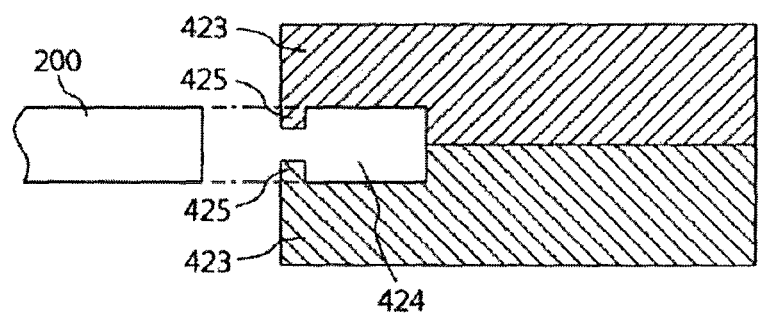
FIGS. 9A to 9C are cross-sectional views illustrating the fixing part of FIGS. 8A to 8C.
Figure 9B:
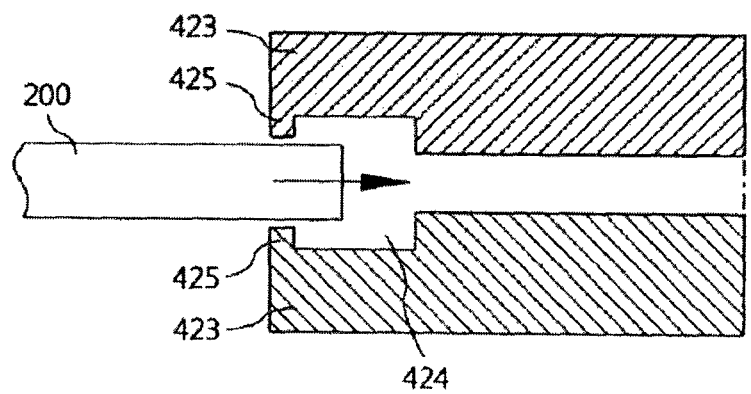
Figure 9C:
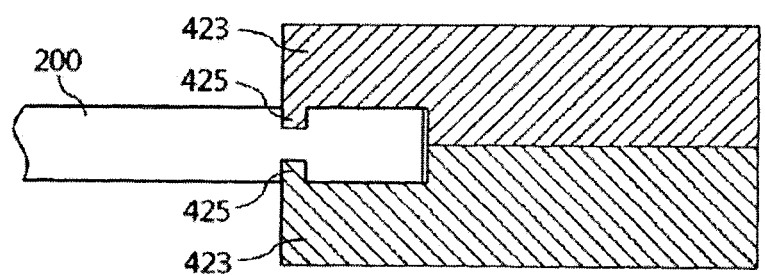

The fixing part 420 may have various structures. FIGS. 8A to 8C are perspective views illustrating a fixing part of a collecting position controller according to another example embodiment of the present invention. FIGS. 9A to 9C are cross-sectional views illustrating the fixing part of FIGS. 8A to 8C. Referring to FIGS. 8A to 8C, the fixing part 420 includes at least two divided subparts 423 that may be divided in a radial direction with respect to an extending direction of the collector 200 as an axis. The divided subparts 423 may be spaced apart from each other in the radial direction. In FIGS. 8A to 8C, the supporting part 410 is omitted. However, the divided subparts 423 are combined with the supporting part 410 to be transported in various methods such as sliding. The divided subparts 423 are combined to form the fixing part 420 having a receiving portion 424. Referring to FIGS. 9A to 9C, a hook 425 may be protruded at an entry of the receiving portion 424.

According to the present example embodiment, the divided subparts 423 are separated as shown in FIGS. 8A to 8C and 9A. The collector 200 is disposed in a position corresponding to the receiving portion 424 as shown in FIGS. 8A to 8C and 9B. The divided subparts 423 are combined as shown in FIGS. 8A to 8C and 9C. The hook 425 holds the collector 200 to fix the collector 200. The receiving portion 424 may have substantially equal to or smaller diameter than the collector 200, so that the collector 200 is tightly clamped to be fixed. Thus, the hook 425 holds the collector 200 to hook the collector 200, so that the tension that pulls the collector 200 in the opposite sides are effectively applied by the collecting position controller 400.

When the collector 200 includes strong material such as metal, the hook 425 may not hold the collector 200 or may deform the collector 200. Thus, when the collector 200 includes the strong material, the collector 200 may have a recess corresponding to the hook 425.

In the above-mentioned example embodiments, the fixing structure of the collecting position controller 400 is explained. However, the collecting position controller 400 may have various fixing structures. In the various fixing structure, the collecting position controller 400 strongly fixes the collector 200 and the tension may be effectively applied to the both sides of the collector 200. Also, the collector 200 may be rotatable.

A scaffold 5000 manufactured by using the above-mentioned apparatus 1000 for manufacturing the scaffold will be explained. FIGS. 10 to 13 are perspective views illustrating tube shaped scaffolds manufactured by an apparatus for manufacturing a scaffold according to one example embodiment of the present invention.

Figure 10:
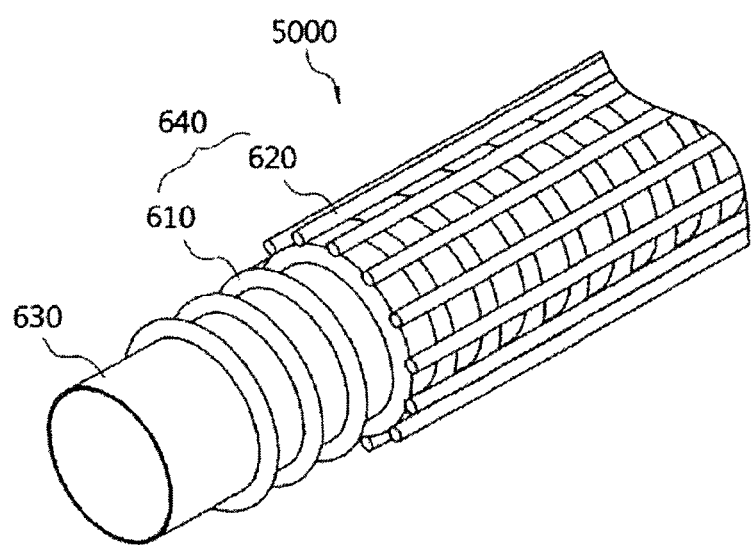
FIGS. 10 to 13 are perspective views illustrating tube shaped scaffolds manufactured by an apparatus for manufacturing a scaffold according to one example embodiment of the present invention.
Figure 11:
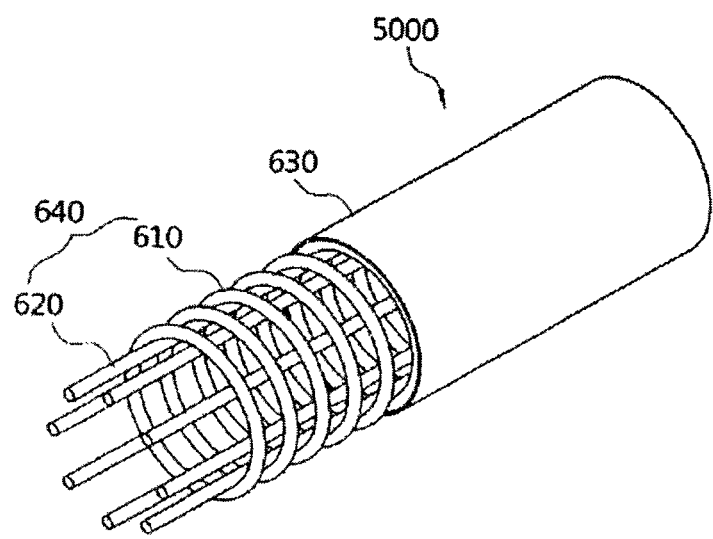
Figure 12:
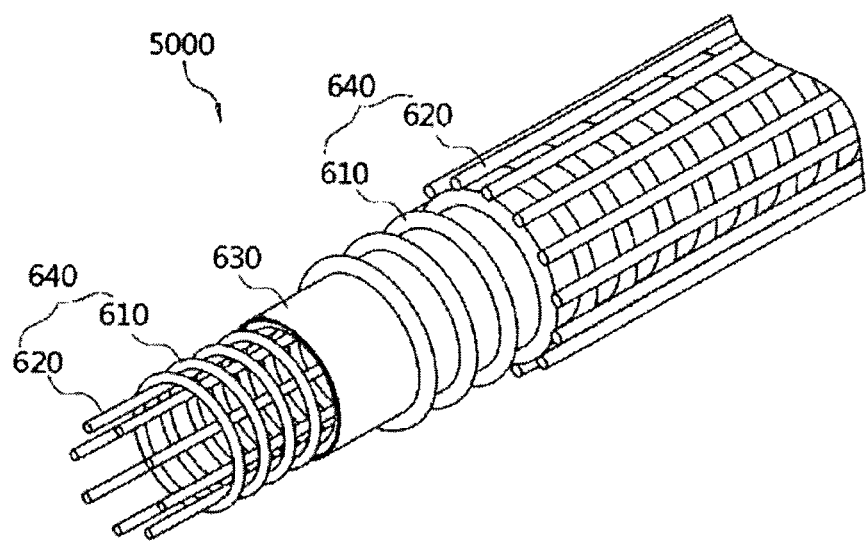
Figure 13:
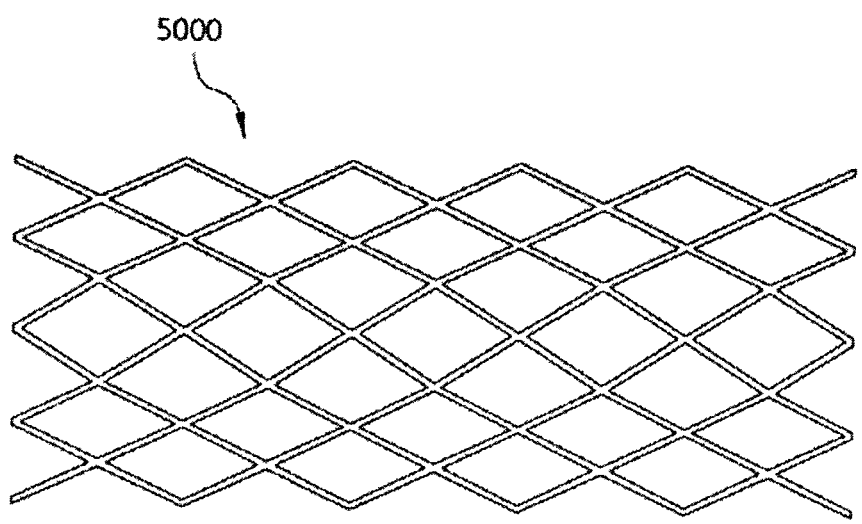

According to one example embodiment of manufacturing the tube shaped scaffold, the apparatus 1000 for manufacturing the scaffold may manufacture various scaffolds 5000 having various diameters, shapes, etc. Also, a tube shaped scaffold having a mono layer of strand may be manufactured by using the apparatus 1000 for manufacturing the scaffold. In FIGS. 10 to 12, a scaffold 5000 having a plurality of layers of strand overlapped along radial and X directions of the collector 200 and having different shapes.

The scaffold 5000 may include a first layer 610 of strand, a second layer 620 of strand and a third layer 630 of strand. The first layer 610 of strand is continuously or intermittently formed along an outer surface of the collector 200 along the radial direction of the collector 200. The second layer 620 of strand is formed along the outer surface of the collector 200 as a plurality of linear shapes in an X direction. The linear shapes of the second layer 620 of strand are spaced apart from each other by a constant interval. The third layer 630 of strand is formed along the outer surface of the collector 200 as a layer shape.

In FIG. 10, the first layer 610 of strand is overlapped with the second layer 620 of strand to form a net type dispensed portion 640 along the outer surface of the third layer 630 of strand. The scaffold 5000 of FIG. 10 may be used for formation of a tear duct.

In FIG. 11, the first layer 610 of strand is overlapped with the second layer 620 of strand to form a net type dispensed portion 640 along an inner surface of the third layer 630 of strand.

In FIG. 12, a plurality of net type dispensed portions 640 that are formed by overlapping of the first and second layers 610 and 620 of strands are formed on the inner surface and the outer surface of the third layer 630 of strand. The scaffold of FIG. 12 may be used for formation of a vessel. One of the net type dispensed portions 640 formed on the inner surface of the third layer 630 of strand is used for formation of an inside skin. Another of the net type dispensed portions 640 formed on the outer surface of the third layer 630 of strand is used for formation of an outside skin. The third layer 630 of strand divides cells of the inside skin from cells of the outside skin during cultivation of the cells.

The scaffold 5000 may have various shape such as zigzag shape, ripple shape, etc. Also, the scaffold 5000 may be formed by various mixtures of the first to third type dispensed portions 610, 620 and 630. The scaffold 5000 may be used in various fields.

In the apparatus 1000 for manufacturing the scaffold, the dispensing head 100 is uniformly transported in the X direction and dispenses melted bio materials (polymer) while the collector 200 is rotated in a uniform speed. Thus, the first layer 610 of strand is formed. In order to form the second layer 620 of strand, the dispensing head 100 is transported in the X direction and dispenses the melted bio materials (polymer) on the collector 200 while the collector 200 is not rotated. The collector 200 is then rotated by a constant angle. And then the dispensing head 100 is transported in the X direction, again. The above-mentioned processes are repeated to form the second layer 620 of strand. In order to form the third layer 630 of strand, the dispensing head 100 dispenses the melted bio materials (polymer) and is transported in the X direction while the collector 200 is rotated at a uniform speed. The above-mentioned processes are examples for forming the first to third type dispensed portions 610, 620 and 630. The first to third type dispensed portions 610, 620 and 630 may be formed in various processes.

The apparatus 1000 for manufacturing the scaffold may also manufacture various typed scaffold 5000 having different shapes from those of FIGS. 10 to 12. That is, bio compatible material is stored in the liquid storing part 110 of the apparatus 1000 for manufacturing the scaffold. The bio compatible material is liquidized by a heating part 130. The liquefied bio compatible material is dispensed onto the collector 200 to form the scaffold 5000 for stents having various shapes. The scaffold 5000 may be used for the stent that extends a narrowed vessel. Alternatively, a plurality of the scaffold 5000 of FIG. 13 may be overlapped to form a mono layered structure or a multi layered structure of strand. The scaffold 5000 may have a mixed structure of various shapes. Also, the scaffold 5000 may have various shapes such as a zigzag shape, a ripple shape, etc.

Thus, the apparatus 1000 for manufacturing the scaffold may manufacture various scaffolds 5000 having various shapes. The scaffolds 5000 manufactured by the apparatus 1000 for manufacturing the scaffold may be used for the vessel, the nerve, the tear duct, the stent, etc.

The foregoing is illustrative of the present teachings and is not to be construed as limiting thereof. Although a few exemplary embodiments have been described, those skilled in the art will readily appreciate from the foregoing that many modifications are possible in the exemplary embodiments without materially departing from the novel teachings and advantages of the present disclosure of invention. Accordingly, all such modifications are intended to be included within the scope of the present teachings. In the claims, means-plus-function clauses are intended to cover the structures described herein as performing the recited function and not only structural equivalents but also functionally equivalent structures.

What is claimed is:

1. An apparatus for manufacturing a scaffold, comprising:
   a dispensing head including:
      a liquid storing part that stores melted bio materials comprising a polymer,
      a nozzle part dispensing the melted bio materials supplied from the liquid storing part, and
      a heating part controlling a temperature of the melted bio materials stored in the liquid storing part;
   a collector having a cylindrical shape, the collector being disposed under the dispensing head to collect the melted bio materials dispensed through the nozzle part;
   a dispensing position controller transporting the dispensing head or the collector in a direction selected from the group consisting of an X direction, a Y direction and a Z direction to control a dispensing position; and
   a collecting position controller including:
      a pair of supporting parts spaced apart from each other in an extending direction of the collector,
      a pair of fixing parts disposed on the pair of supporting parts, respectively, the pair of fixing parts holding and fixing both ends of the collector,
      a transporting part that transports at least one of the pair of supporting parts in the extending direction of the collector, and
      a rotating part disposed at least one of the pair of fixing parts to rotate the collector along the extending direction as an axis.

2. The apparatus for manufacturing the scaffold of claim 1, wherein
   the pair of fixing parts of the collecting position controller hold and fix the both ends of the collector, and
   the transporting part transports at least one of the pair of supporting parts so that a distance between the pair of supporting parts is increased along the extending direction of the collector, and so that a pulling tension is applied to the collector in the extending direction and the both ends of the collector are held and fixed.

3. The apparatus for manufacturing the scaffold of claim 1, wherein
   each of the pair of supporting parts of the collecting position controller is protruded in the extending direction of the collector to form a receiving portion having an empty space, and
   each of the pair of fixing part includes:
      a collet having one side, into which the collector is inserted, and another side received in and supported by the receiving portion; and
      a clamper supporting the one side of the collet and combined with the receiving portion so that the collet is received in and fixed to the receiving portion, and so that the collector is inserted into the collet and the receiving portion is combined with the clamper, thereby fixing and holding the collector.

4. The apparatus for manufacturing the scaffold of claim 3, wherein
a receiving screw is formed on an outer surface of the receiving portion of the collecting position controller,
a clamping screw corresponding to the receiving screw is formed on an inner surface of the clamper corresponding to the receiving portion, and
the receiving screw is combined with the clamping screw by a screw combination, thereby combining the receiving portion to the clamper.

5. The apparatus for manufacturing the scaffold of claim 4, wherein
the one side of the collet of the collecting position controller includes a collet head having a cross-sectional diameter that decreases as a distance from a periphery is decreased to form a tapered shape, and a clamping tapered portion formed on an inner surface of an opposite side to the receiving portion of the clamper, and having an inclined inner surface corresponding to the collet head,
the another side of the collet includes a collet tail of which a diameter of an inner surface is decreased, as a distance from the periphery is decreased, and a receiving tapered portion formed on an inner surface of the receiving portion and having an inclined surface corresponding to the collet tail, and
the collet head and the collet tail are pressed to make contact with the clamping tapered portion and the receiving tapered portion, respectively, when the receiving portion is combined with the clamper so that the collet is compressed.

6. The apparatus for manufacturing the scaffold of claim 1, wherein each of the pair of fixing parts of the collecting position controller comprises at least two divided subparts that are dividable in a radial direction with respect to an extending direction of the collector as an axis,
the divided subparts are combined to form the fixing part having a receiving portion, and a hook is protruded at an entry of the receiving portion, and
the collector is disposed in a position corresponding to the receiving portion while the divided subparts are separated, and then the divided subparts are combined so that the hook holds the collector to fix the collector.

7. The apparatus for manufacturing the scaffold of claim 6, wherein the receiving portion has a diameter substantially equal to or smaller than the collector.

8. The apparatus for manufacturing the scaffold of claim 6, wherein the collector has a recess corresponding to the hook.

9. The apparatus for manufacturing the scaffold of claim 1, wherein the collecting position controller fixes the collector that has a ratio of diameter to length to be about 0.05 to about 0.5.

10. The apparatus for manufacturing the scaffold of claim 1, wherein the liquid storing part stores melted or liquefied bio compatible materials.

11. The apparatus for manufacturing the scaffold of claim 1, wherein the collector is replaceable with another collector having a different diameter.

12. The apparatus for manufacturing the scaffold of claim 1, further comprising a controller connected to the dispensing position controller to control dispensing position, and connected to the collecting position controller to control speed of rotation of the fixing part.

* * * * *